(12) United States Patent
Di Biase

(10) Patent No.: US 12,721,947 B2
(45) Date of Patent: Sep. 1, 2026

(54) ADAPTIVE METHOD AND SYSTEM FOR A PERSONALIZED DAILY INFUSION THERAPY OF PARKINSON'S DISEASE

(71) Applicant: Brain Innovations, S.r.l., Rome (IT)

(72) Inventor: Lazzaro Di Biase, Rome (IT)

(73) Assignee: Brain Innovations, S.r.l., Rome (IT)

( * ) Notice: Subject to any disclaimer, the term of this patent is extended or adjusted under 35 U.S.C. 154(b) by 695 days.

(21) Appl. No.: 18/025,049

(22) PCT Filed: May 25, 2021

(86) PCT No.: PCT/IT2021/050159

§ 371 (c)(1),
(2) Date: Mar. 7, 2023

(87) PCT Pub. No.: WO2022/054111

PCT Pub. Date: Mar. 17, 2022

(65) Prior Publication Data

US 2023/0321348 A1 Oct. 12, 2023

(30) Foreign Application Priority Data

Sep. 10, 2020 (IT) ........................ 102020000021379

(51) Int. Cl.
*A61M 5/172* (2006.01)
*G16H 20/17* (2018.01)
(Continued)

(52) U.S. Cl.
CPC .......... *A61M 5/1723* (2013.01); *G16H 20/17* (2018.01); *G16H 40/67* (2018.01); *G16H 50/30* (2018.01);
(Continued)

(58) Field of Classification Search
CPC ........ A61M 5/1723; A61M 2205/3303; A61M 2205/3306; A61M 2205/3375;
(Continued)

(56) References Cited

U.S. PATENT DOCUMENTS

| | | | | |
|---|---|---|---|---|
| 5,711,316 A * | 1/1998 | Elsberry | A61M 5/1723 600/595 |
| 2009/0062686 A1* | 3/2009 | Hyde | A61B 5/7435 600/587 |
| 2014/0257047 A1* | 9/2014 | Sillay | H04L 63/10 600/595 |

FOREIGN PATENT DOCUMENTS

| | | | |
|---|---|---|---|
| JP | 2004000496 A * | 1/2004 | A61M 5/14276 |
| JP | 2014506113 A | 3/2014 | |

(Continued)

OTHER PUBLICATIONS

Sasa Bastinos, Ana, "International Search Report and Written Opinion of the International Searching Authority for International Application No. PCT/IT2021/050159," European Patent Office, Sep. 2, 2021.

(Continued)

*Primary Examiner* — Lauren P Farrar
(74) *Attorney, Agent, or Firm* — Florek & Endres PLLC

(57) ABSTRACT

A method and a system are described, for managing an infusion therapy in the Parkinson's disease, through the analysis of the motion status of patients, wherein the motion status can be in one of the following phases: OFF phase, wherein Parkinson's symptoms, such as rigidity, tremor and bradykinesia, emerge; ON phase wherein the symptoms markedly improve; DIS phase wherein involuntary movements emerge, called dyskinesias; as detectors of the symptoms the following parameters are used: voice analysis; face analysis; tremor analysis; movement analysis; levodopa and metabolite levels of monoamines in the sub-cutaneous inter-
(Continued)

stitial liquid of the patients; an algorithm being provided, which automatically modifies the infusion rate of a drug during the day, the infusion rate being computed by using the parameters as detectors.

2 Claims, 2 Drawing Sheets

(51) Int. Cl.
*G16H 40/67* (2018.01)
*G16H 50/30* (2018.01)

(52) U.S. Cl.
CPC ............... *A61M 2205/3303* (2013.01); *A61M 2205/3306* (2013.01); *A61M 2205/3375* (2013.01); *A61M 2230/63* (2013.01)

(58) Field of Classification Search
CPC ... A61M 2230/63; G16H 20/17; G16H 40/67; G16H 50/30; G16H 10/60; G16H 40/60; G16H 50/20; A61B 5/4082; A61B 5/4839; A61B 5/11; A61B 5/14525; A61B 5/681
See application file for complete search history.

(56) References Cited

FOREIGN PATENT DOCUMENTS

| | | | |
|---|---|---|---|
| JP | 2020510909 | A | 9/2020 |
| WO | 2006105621 | A1 | 10/2006 |
| WO | 2018220085 | A1 | 12/2018 |
| WO | 2019/157421 | A1 | 8/2019 |

OTHER PUBLICATIONS

Goud K. Yugender et al., "Wearable Electrochemical Microneedle Sensor for Continuous Monitoring of evodopa: Toward Parkinson Management", ACS Sensors, vol. 4, No. 8, Aug. 23, 2019 (Aug. 23, 2019), p. 2196-2204, XP055799216, DOI: 10.1021/acssensors.9b01127, ISSN:2379-3694.

Sharma Vinod et al, "SPARK: Personalized Parkinson Disease Interventions through Synergy between a Smartphone and a Smartwatch", Jun. 22, 2014 (Jun. 22m 2014), ICIAP: International Conference On Image Analysis and Processing, 17th International Conference, Naples, Italy, Sep. 9-13, 2013. Proceedings; [Lecture Notes in Computer Science; Lect.Notes Computer], Springer, Berlin, Heidelberg, pp. 103-1, XP047339905, ISBN: 9783642173189.

Andong Zhan et al, "High Frequency Remote Monitoring of Parkinson's Disease via Smartphone: Platform Overview and Medication Response Detection", arxiv.org, Cornell University Library, 201 Olin Library Cornell University Ithaca, NY 14853, Jan. 5, 2016 (May 5, 2016), XP080960534.

Anonymous, "Managing PD Mid-Strinde. A Treatment Guide to Parkinson's Disease", Dec. 31, 2018 (Dec. 31, 2018), Retrieved from the Internet: URL:https://www.parkinson.org/sites/default/files/attachments/MidStride.pdf XP055800016 [retrieved on Apr. 29, 2021].

Brognara Lorenzo et al., "Assessing Gait in Parkinson's Disease Using Wearable Motion Sensors: A Systematic Review", Diseases, vol. 7, No. 1, Feb. 5, 2019 (Feb. 5, 2019), XP055800539 DOI: 10.3390/diseases7010018.

Anonymous, "Monoamine neurotransmitter—Wikipedia", Jul. 11, 2020 (Jul. 11, 2020), Retrieved from the Internet: URL:https://en.wikipedia.org/w/index.php?title=Monoamine_neurotransmitter&oldid=967153184 XP055800533 [retrieved on May 30, 2021].

* cited by examiner

ADAPTIVE METHOD AND SYSTEM FOR A PERSONALIZED DAILY INFUSION THERAPY OF PARKINSON'S DISEASE

The present invention relates to a method and an adaptive system for modulating the infusion therapy of Parkinson's disease.

The invention is part of the technical field of medicine, in particular neurology.

Parkinson's disease is the most frequent neurodegenerative disease after Alzheimer's disease. The diagnosis of Parkinson's disease is essentially clinical and currently based on the objective and anamnestic identification of the characteristic signs and symptoms of the disease and on the exclusion of any atypical symptoms.

Patients with Parkinson's disease can experience fluctuations in their motor status during the day going from an OFF phase, in which parkinsonian symptoms such as rigidity, tremor and bradykinesia emerge, to an ON phase in which these symptoms improve significantly, marked with a phase characterized by involuntary movements called dyskinesias (DIS). These fluctuations are due to fluctuations in dopamine levels in the central nervous system. The drug used to improve the motor symptoms of Parkinson's disease is levodopa, which is converted in the central nervous system to dopamine. Motor fluctuations consist of an initial benefit on motor symptoms after the administration of a dose of levodopa (time in motor ON) followed by a return of parkinsonian symptoms, such as slowing of movements, rigidity or tremor (time in motor OFF) that lasts until at the beginning of the benefit of the next dose. These fluctuations lead to a continuous oscillation of the patient's motor performance during the day, with an alternation of motor ON states, in which parkinsonian symptoms are well controlled by motor OFF therapy, in which parkinsonian symptoms re-emerge. Dyskinesias, on the other hand, are involuntary movements induced by levodopa. An increase in Levodopa doses can reduce motor OFF times, but tends to increase dyskinesias, while a reduction in levodopa doses can reduce dyskinesias, but tends to increase motor OFF time. In these patients, continuous administration systems of levodopa or dopamine agonists can be used, however it may be difficult to set a drug infusion rate that is able to satisfactorily control the total time in motor OFF without inducing dyskinesias.

Methods of adaptive therapy are known that modulate the therapy conveyed through Deep Brain Stimulation, DBS.

Conventional DBS consists of the surgical implantation of two electrodes within a specific area of the brain (subthalamic nucleus or internal pale globe). Electrodes which are then connected with thin cables to a small stimulator placed under the skin near the collarbone.

However, this method has shown some limitations. First of all, the stimulation is constantly delivered to the patient's brain, with an intensity, therefore, not always suited to his needs.

This fact occurs because, in the advanced stages, the symptoms of Parkinson's disease are fluctuating. In a few seconds we pass from motor block to very disabling involuntary movements.

To overcome this limitation, an adaptive DBS has been developed, i.e. a stimulation that adapts automatically and in real time to the patient's clinical status. In other words, the electrical stimulus varies according to the brain activity detected moment by moment. In this way it is always calibrated to the patient's status.

However, adaptive DBS uses the measurement of brain activity as the only parameter to modulate the therapy and this fact does not allow the patient's motor condition to be correctly identified. It is also highly invasive, as it requires the insertion of electrodes into the subthalamic nucleus or the internal pale globe.

Object of the present invention is providing a method, and a system for implementing said method, respectively in accordance with claims 1 and 2, to modulate infusion therapy using the data of the initial therapeutic scheme as feedback.

The method for managing the infusion therapy of Parkinson's disease, called management taking place through the analysis of the motor state of patients suffering from said Parkinson's disease, in which said motor state may be in one of the following phases:

- OFF phase, in which parkinsonian symptoms such as rigidity, tremor and bradykinesia emerge;
- ON phase, in which said symptoms improve markedly;
- DIS phase, in which involuntary movements defined as dyskinesias emerge;

is characterized by using the following parameters as detectors of said symptoms:

- voice and facial analysis;
- analysis of tremor and movement;
- Levodopa and monoamine metabolites levels in the subcutaneous interstitial fluid of said patients;

since an algorithm is provided that automatically modifies the drug infusion rate during the day, said infusion rate being calculated using these parameters as detectors.

The system for the management of infusion therapy of Parkinson's disease includes:

- an electronic bracelet, equipped with an accelerometer, a magnetometer and a triaxial gyroscope, used to collect continuous data on tremor and movement;
- a camera to capture facial expressions, to be activated at the request of the patient;
- a recorder, to record the patient's voice, to be activated at the request of the patient;
- a micro-dialysis pump, connected to an analyzer unit and a subcutaneous needle, designed to collect and analyze samples of interstitial fluid to determine the levels of levodopa and monoamine metabolites in said subcutaneous interstitial fluid;
- a processing device, equipped with suitable software which, using a movement stabilization algorithm, designed to integrate movement, tremor, facial, vocal data and the levels of levodopa and monoamine metabolites in said subcutaneous interstitial fluid, calculates the drug infusion rate necessary to maintain the motor state ON, using the data of the initial therapeutic scheme as feedback;
- an electronic interface, connected with said processing device, designed to change the drug infusion rate with the new speed calculated by said movement stabilization algorithm.

According to a preferred embodiment, the camera, the recorder, the processing device and the relative software are integrated in a palmtop/smartphone.

In practice, the drug infusion rate is modified using as feedback data from the initial therapeutic scheme, analysis of movement, tremor, facial, vocal, and levels of levodopa and monoamine metabolites in the subcutaneous interstitial fluid.

The advantage of this device is that, through multiparametric monitoring (motor, tremor, vocal, facial, biochemical), it guarantees the patient to maintain an optimal motor performance (state of motor ON) continuously, by varying the drug infusion rate according to a personalized therapeutic scheme, which varies according to fluctuations in motor performance, avoiding states of motor OFF and dyskinesias.

Furthermore, the system is minimally invasive.

It will be immediately obvious that innumerable variations and modifications (for example relating to shape, dimensions, arrangements and parts with equivalent functionality) can be made to what is described without departing from the scope of the invention, as appears from the attached claims.

It is understood that all attached claims form an integral part of the present description.

The present invention will be better described by a preferred embodiment, given by way of non-limiting example, with reference to the attached drawings, in which.

Figure 1:
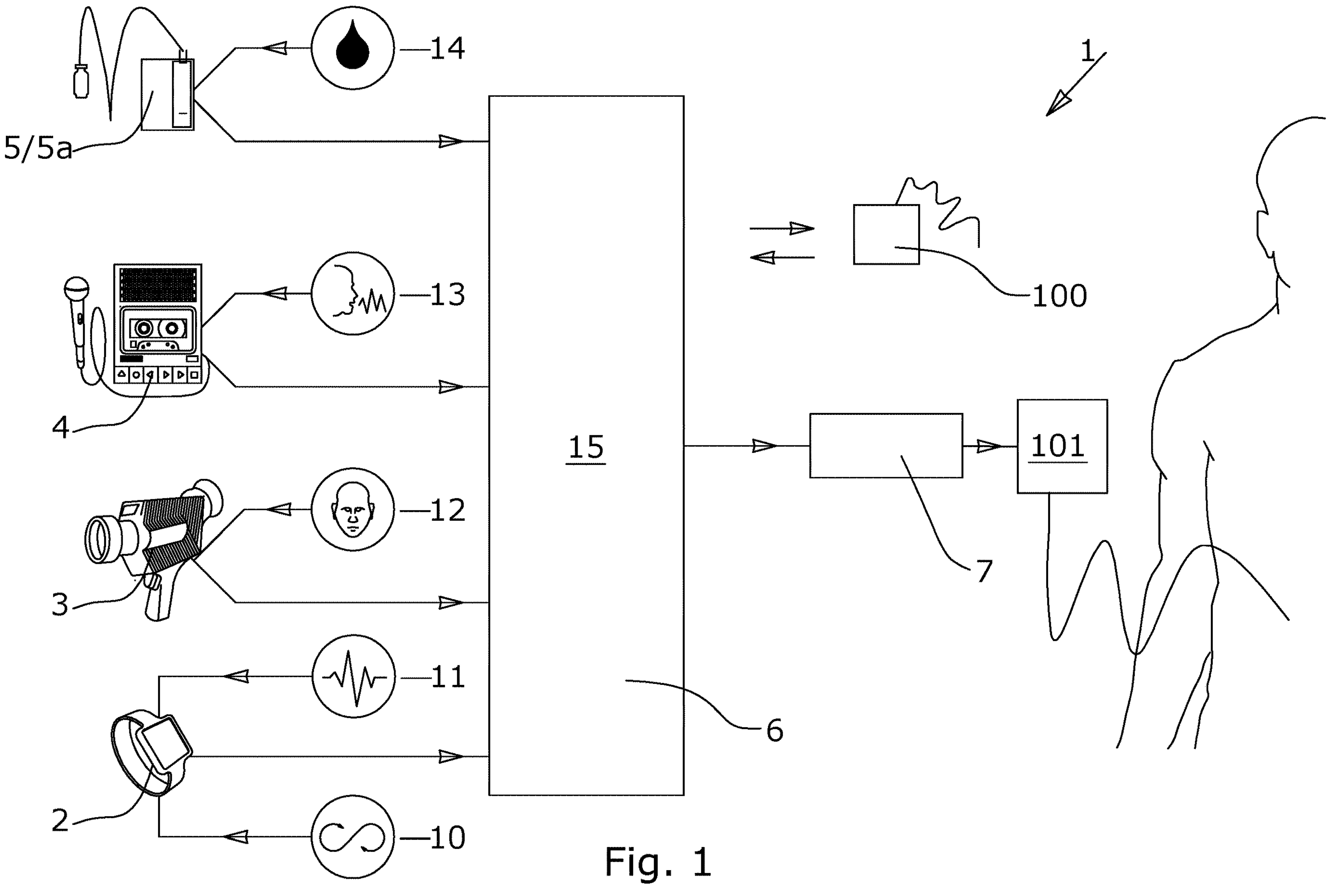
FIG. 1 shows a system for the management of infusion therapy in Parkinson's disease, according to the invention.

With reference to FIG. 1, the system (1) for the management of infusion therapy in Parkinson's disease includes:

- an electronic bracelet (2), equipped with an accelerometer, a magnetometer and a triaxial gyroscope, used to continuously collect data on tremor and movement;
- a camera (3) for recording facial expressions, to be activated at the request of the patient;
- a recorder (4) for recording the voice, to be activated at the request of the patient;
- a micro-dialysis pump (5) connected to an analyzer unit (5*a*) and with a subcutaneous needle for the collection of samples of interstitial fluid to determine the levels of levodopa and monoamine metabolites in said subcutaneous interstitial fluid;
- a processing device (6), equipped with suitable software which, using a movement stabilization algorithm designed to integrate movement, tremor, facial, vocal data and the levels of levodopa and monoamine metabolites in said subcutaneous interstitial fluid, calculates the drug infusion rate necessary to maintain the motor state ON, using the data of the initial therapeutic scheme as feedback (100);
- an electronic interface (7) that modifies the drug infusion rate, with the new speed calculated by said movement stabilization algorithm.

Starting from said initial therapy (100), established on the basis of the symptoms observed, the functioning of the system (1), to modulate the therapy according to the course of the disease, is divided into the following steps.

Step 1—The electronic bracelet (2) continuously records the patient's movement (10) and tremor (11) data.

Step 2—When the patient perceives a state of OFF or marked dyskinesias (DIS), he uses the camera (3) to record facial expressions (12) and the recorder (4) to record his voice (13). At the same time, the analyzer unit (5*a*) detects the levels of levodopa and monoamine metabolites (14) in the interstitial fluid samples taken from the micro-dialysis pump (5) through said subcutaneous needle.

Step 3—The processing device (6) receives the combined data from the electronic bracelet (2), the camera (3), the recorder (4) and the analyzer unit (5*a*) connected to the micro-dialysis pump (5) of movement (10), tremor (11), facial images (12), voice (13) and levels of levodopa and monoamine metabolites (14) and, through the movement stabilization algorithm (15), determines the new drug infusion rate (101). Finally, the drug infusion rate is modified through said electronic interface (7).

Figure 2:
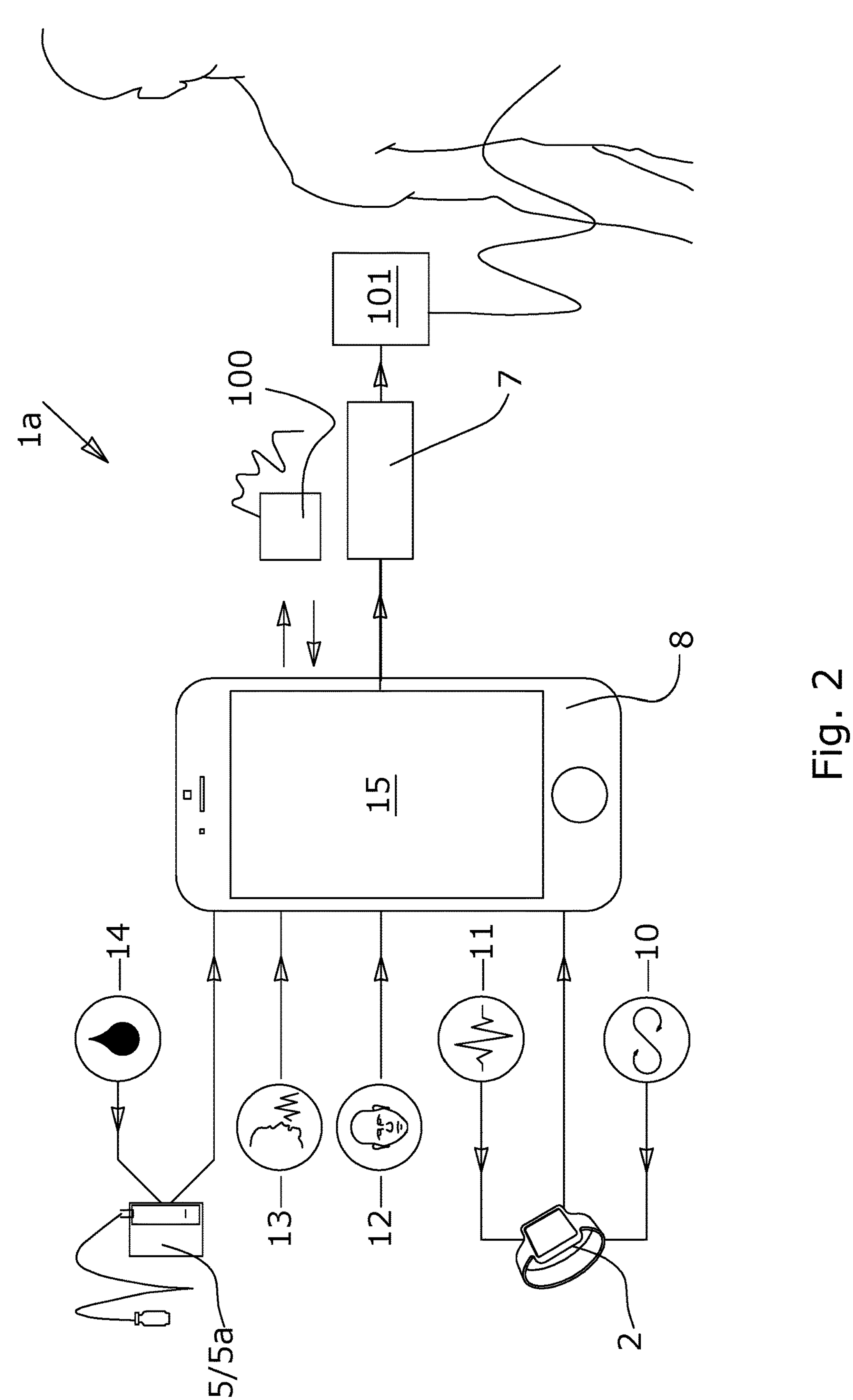
FIG. 2 shows a variant of the system according to the invention.

According to a preferred embodiment (1*a*), shown in FIG. 2, the camera (3), the recorder (4), the processing device (6) and the related software are integrated in a PDA/smartphone (8), so that the electronic bracelet (2) and the analyzer unit (5*a*) connected to the micro-dialysis pump (5), send the analysis data of movement (10) and tremor (11) and levels of levodopa and monoamine metabolites (14) directly to the PDA/smartphone (8), which will send to the electronic interface (7) the instructions for modifying the drug infusion rate, with the new rate (101) calculated by said movement stabilization algorithm.

The drug infusion rate (101), modified in real time according to the course of the disease, will substantially maintain a motor state of ON, without motor OFF or dyskinesias.

The invention claimed is:

1. A system for managing an infusion therapy for the treatment of Parkinson's disease, said management occurring through a determination of a motor status of patients affected by said Parkinson's disease, wherein said motor status can be in one of the following phases:

- OFF phase, where Parkinson's symptoms of rigidity, tremor and bradykinesia, emerge;
- ON phase where said Parkinson's symptoms markedly improve;
- DYS phase where involuntary movements, called dyskinesias, emerge;
- wherein said analysis uses as detectors of said symptoms the following parameters: voice analysis; face analysis; tremor analysis; movement analysis; and levodopa and metabolite levels of monoamines in the sub-cutaneous interstitial liquid of said patients;
- said system comprising:
  - an electronic bracelet, equipped with an accelerometer, a magnetometer and a gyroscope, three-axial, for collecting data continuously about tremor and movement;
  - a photo-camera to shoot face expressions, to be actuated upon request of a patient;
  - a recorder to record the patient voice, to be actuated upon request of the patient;
  - a micro-dialysis pump connected to an analysing unit and to a sub-cutaneous needle, adapted to collect and analyse samples of interstitial liquid to determine the levodopa and metabolite levels of the monoamines in said sub-cutaneous interstitial liquid;
  - a processing device, equipped with a suitable software which, using a movement stabilizing algorithm, adapted to integrate data about movement, tremor, face, voice and levodopa and metabolite levels of monoamines in said sub-cutaneous interstitial liquid, computes an infusion rate of a drug necessary to keep an ON motor status, using as feedback data about a starting therapeutic scheme;
  - an electronic interface, connected to said processing device, adapted to modify the infusion rate of the drug with a new rate computed by said movement stabilizing algorithm.

2. The system for managing an infusion therapy for the treatment of Parkinson's disease according to claim 1, wherein said photo-camera, said recorder, said processing device and related software are integrated in a handheld computer/smartphone, so that the electronic bracelet and the analysing unit send analysis data about movement, tremor and levodopa and metabolite levels of monoamines directly to said handheld computer/smartphone.

* * * * *